United States Patent [19]

Long

[11] Patent Number: 5,068,249

[45] Date of Patent: Nov. 26, 1991

[54] AQUEOUS RANITIDINE COMPOSITIONS STABILIZED WITH ETHANOL

[75] Inventor: David R. Long, Royston, England

[73] Assignee: Glaxo Group Limited, London, England

[21] Appl. No.: 494,804

[22] Filed: Mar. 14, 1990

Related U.S. Application Data

[63] Continuation of Ser. No. 344,620, Apr. 28, 1989, abandoned, which is a continuation of Ser. No. 131,442, Dec. 11, 1987, abandoned.

[30] Foreign Application Priority Data

Dec. 12, 1986 [GB] United Kingdom ............... 86 29781

[51] Int. Cl.$^5$ .............................................. A61K 31/34
[52] U.S. Cl. .................................................. 514/471
[58] Field of Search ................................ 514/461, 471

[56] References Cited

FOREIGN PATENT DOCUMENTS 2547727 12/1984 France .
2120938  5/1983 United Kingdom .
2142820  1/1985 United Kingdom .

OTHER PUBLICATIONS

Chem. Abst. (97)–61014G (1982).
Chem. Abst. (104)–102280Z (1986).

Primary Examiner—Frederick E. Waddell
Assistant Examiner—Diane Gardner
Attorney, Agent, or Firm—Bacon & Thomas

[57] ABSTRACT

The stability of aqueous formulations of ranitidine or a physiologically acceptable salt thereof is enhanced by the addition of ethanol.

12 Claims, No Drawings

AQUEOUS RANITIDINE COMPOSITIONS STABILIZED WITH ETHANOL

This application is a continuation of application Ser. No. 07/344,620, filed Apr. 28, 1989, now abandoned, which is a continuation of Ser. No. 07/131,442, filed Dec. 11, 1987, now abandoned.

The present invention relates to a pharmaceutical composition containing as active ingredient the histamine $H_2$ antagonist ranitidine.

Ranitidine, [N-[2-[[[5-(dimethylamino)methyl-2-furanyl]methyl]thio]ethyl]-N'-methyl-2-nitro-1,1-ethenediamine, and its physiologically acceptable salts are described in British Patent Specification No. 1565966. In that specification there is reference to liquid formulations for oral and parenteral administrations and there is a description of an aqueous based formulation for intravenous use and another of an oral syrup. Both of these formulations contained sufficient hydrochloric acid to achieve a pH of 5.0 and the syrups also contained Sorbitol solution BPC and a flavour as required.

British Patent Application No. GB 2142820A describes aqueous based formulations containing ranitidine and/or one or more of its physiologically acceptable salts thereof having a pH within the range 6.5-7.5. In that specification there is reference to liquid formulations for oral and parenteral administration and there are examples of aqueous formulations for intravenous and oral use. These formulations contain ranitidine hyrochloride and are buffered to a pH of approximately 7 and for intravenous administration the formulations also contain phenol or sodium chloride. For oral administration the formulation also contains hydroxypropylmethyl cellulose as a viscosity enhancing agent, a preservative (parabens), a sweetening agent and a flavour. These compositions have a significantly greater shelf-life over those in British Patent No. 1565966.

We have now suprisingly found that the stability of ranitidine in aqueous based formulations and more particularly aqueous based formulations for oral administration may be substantially enhanced by the addition of ethanol to the formulation.

Thus the present invention provides a pharmaceutical composition which is an aqueous formulation of ranitidine and/or one or more physiologically acceptable salts thereof also containing ethanol. The aqueous formulation is prepared using ingredients of a purity such that it is suitable for administration to patients and will in general contain at least one conventional pharmaceutical excipient in addition to the ethanol and ranitidine and/or physiologically acceptable salts thereof.

The amount of ethanol present in the formulation is such that the resulting formulation has the enhanced stability. Preferably the amount of ethanol in the composition on a weight/volume basis of the complete formulation, is within the range 2.5% to 10%, and more particularly is between 5 to 10% w/v, more especially 7-8% w/v.

Preferred compositions according to the invention are those in which the pH of the aqueous formulation is within the range 6.5 to 7.5, particularly 6.8 to 7.4 and more especially 7 to 7.3. The required pH of the formulation is preferably obtained by the use of suitable buffer salts for example, potassium dihydrogen orthophosphate and disodium hydrogen orthophosphate or citric acid and disodium hydrogen orthophosphate.

A preferred embodiment of the invention is an aqueous formulation for oral administration. Such a formulation may comprise ranitidine and/or one or more of its physiologically acceptable salts dissolved in water, ethanol, a preservative and a viscosity enhancing agent. Preferably the required pH of the formulation is obtained by the use of appropriate buffer salts. Optionally the composition may also contain other conventional excipients such as a sweetener, a flavour and/or flavouring aids.

Examples of suitable preservatives include on or more alkyl hydroxybenzoates such as methyl, ethyl, propyl and/or butyl hydroxybenzoates.

Examples of suitable viscosity enhancing agents include Xanthan gum, sorbitol glycerol, sucrose or a cellulose derivative such as carboxymethylcellulose or a salt thereof of a $C_{1-4}$ alkyl and/or a hydroxy-$C_{2-4}$alkyl ether of cellulose such as methylcellulose, ethylcellulose, hydroxyethylcellulose, hydroxypropylcellulose, hydroxyethylmethylcellulose and hydroxypropylmethylcellulose.

Examples of suitable sweeteners include saccharin sodium, sodium cyclamate, sorbitol and sucrose.

Examples of suitable flavouring agents include 'mint' flavours such as peppermint flavouring agents.

The concentration of ranitidine in the oral formulation, expressed as free base, is conveniently within the range 20-400 mg per 10 ml, for example 20-200 mg per 10 ml, more particularly 150 mg per 10 ml dose.

The amount of ethanol in the formulation for oral administration, expressed as a percentage of the complete formulation on a weight/volume basis, is preferably within the range 2.5 to 10%, and more particularly between 5 to 10%, more especially 7-8%.

The amount of viscosity enhancing agent in the formulation will preferably be sufficient to give a solution with a viscosity in the range of 10 to 100 centipoises.

The aqueous formulations for oral administration are conveniently prepared by mixing an aqueous solution of ranitidine and/or one or more of its physiologically acceptable salts together with ethanol and the excipients, with aqueous solution or dispersion of the viscosity enhancing agent.

The aqueous formulations according to the invention are preferably prepared using ranitidine in the form of its hydrochloride salt.

An illustrative example of a formulation according to the invention is as follows. In this example the relative proportions of ranitidine hydrochloride and the buffer salts are such that the formulation has a pH of approximately 7.

| Ranitidine oral liquid formulation (150 mg/10 ml) expressed as free base | |
|---|---|
| | % w/v |
| Ranitidine hydrochloride | 1.68 |
| Ethanol | 7.5 |
| Potassium dihydrogen orthophosphate | 0.095 |
| Disodium hydrogen orthophosphate anhydrous | 0.350 |
| Hydroxypropylmethylcellulose | qs |
| Preservative | qs |
| Sweetening agents | qs |
| Flavour | qs |
| Purified water BP to | 100 ml |

I claim:

1. A pharmaceutical composition which is an aqueous formulation for oral administration of an effective amount of ranitidine and/or one or more physiologically acceptable salts thereof, said formulation comprising a stabilizing effective amount of ethanol and said composition having a pH in the range of 6.5-7.5.

2. A pharmaceutical composition according to claim 1 containing 2.5% to 10% weight/volume ethanol based on the complete formulation.

3. A pharmaceutical composition according to claim 1 containing 7% to 8% weight/volume ethanol based on the complete formulation.

4. A pharmaceutical composition according to claim 1 having a pH in the range 6.8 to 7.4.

5. A pharmaceutical composition according to claim 1 having a pH in the range 7.0 to 7.3.

6. A pharmaceutical composition according to claim 1 wherein said pH is obtained by the use of buffer salts.

7. A pharmaceutical composition according to claim 1 prepared using ranitidine in the form of the hydrochloride salt.

8. A pharmaceutical composition as claimed in claim 1, wherein the effective amount is 20-400 mg ranitidine per 10 ml dose expressed as free base.

9. A pharmaceutical composition as claimed in claim 1, wherein the effective amount is 20-200 mg ranitidine per 10 ml dose expressed as free base.

10. A pharmaceutical composition as claimed in claim 1, wherein the effective amount is 150 mg ranitidine per 10 ml dose expressed as free base.

11. A pharmaceutical composition which is an aqueous formulation of ranitidine suitable for oral administration containing 150 mg ranitidine per 10 ml dose expressed as free base, said formulation having a pH in the range 7.0 to 7.3 and also containing 7% to 8% weight/volume ethanol based on the complete formulation.

12. A pharmaceutical composition according to claim 11 wherein said pH is obtained by the use of buffer salts.

* * * * *